US008168202B2

(12) United States Patent
Kapikian et al.

(10) Patent No.: US 8,168,202 B2
(45) Date of Patent: May 1, 2012

(54) HEXAVALENT BOVINE ROTAVIRUS REASSORTANT COMPOSITION DESIGNED FOR USE IN DEVELOPING COUNTRIES

(75) Inventors: Albert Z. Kapikian, Rockville, MD (US); Lone Simonsen, Chevy Chase, MD (US); Timo Vesikari, Tampare (FI); Yasutaka Hoshino, Wheaton, MD (US); David M. Morens, Chevy Chase, MD (US); Robert M. Chanock, Bethesda, MD (US); John R. La Montagne, Alexandria, VA (US); Mary Elaine La Montagne, legal representative, Alexandria, VA (US); Brian R. Murphy, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 739 days.

(21) Appl. No.: 11/994,640

(22) PCT Filed: Jul. 7, 2006

(86) PCT No.: PCT/US2006/027444
§ 371 (c)(1),
(2), (4) Date: Jul. 30, 2008

(87) PCT Pub. No.: WO2007/009081
PCT Pub. Date: Jan. 18, 2007

(65) Prior Publication Data
US 2008/0292660 A1    Nov. 27, 2008

Related U.S. Application Data

(60) Provisional application No. 60/697,435, filed on Jul. 7, 2005.

(51) Int. Cl.
*A61K 39/15* (2006.01)
(52) U.S. Cl. ............... 424/215.1; 424/205.1; 424/202.1; 424/184.1
(58) Field of Classification Search ........................ None
See application file for complete search history.

(56) References Cited

U.S. PATENT DOCUMENTS
2004/0223981 A1  11/2004  Kapikian

FOREIGN PATENT DOCUMENTS
WO    WO 00/06196    *  2/2000
WO    WO 00/06196 A2    2/2000

OTHER PUBLICATIONS

Genbank Accession # AF034852, Human rotavirus DG8 outer capsid protein (VP7) mRNA, complete cds, Sep. 17, 2000.*
Nakata et al., Epidemiological Study of the G Serotype Distribution of Group A Rotaviruses in Kenya From 1991 to 1994, 1999, Journal of Medical Virology, vol. 58, 296-303.*
Kapikian A Z et al: "Jennerian and Modified Jennerian Approach to Vaccination Against Rotavirus Diarrhea Using a Quadrivalent Rhesus Rotavirus (Rrv) and Human-Rrv Reassortance Vaccine" A Archives of Virology, New York, NY, US, vol. 12, 1996, pp. 163-175, XP000872653 ISSN: 0304-8608 abstract.
Hoshino Y et al: "Construction of Four Double Gene Substitution Human X Bovine Rotavirus Reassortant Vaccine Candidates" Journal of Medical Virology, Alan R. Liss, New York, NY, US, vol. 51, No. 4, Apr. 1997, pp. 319-325, XP000872627 ISSN: 0146-6615.
Midthun K et al: "Rotavirus Vaccines: An Overview" Clinical Microbiology Reviews, Washington, DC, US, vol. 9, No. 3, Jul. 1996, pp. 423-434, XP000872603 ISSN: 0893-8512.
Kapikian A Z et al: "Efficacy of a Quadrivalent Rhesus Rotavirus-Based Human Rotavirus Vaccine Aimed at Preventing Severe Rotavirus Diarrhea in Infants and Young Children" Journal of Infectious Diseases, Chicago, IL, US, vol. 174, No. SUPPL 1, Sep. 1996, pp. S65-S72, XP000872623 ISSN: 0022-1899.
Hoshino Y et al: "Construction and characterization of rhesus monkey rotavirus (MMU18006)- or bovine rotavirus (UK)-based serotype G5, G8, G9 or G10 single VP7 gene substitution reassortant candidate vaccines" Vaccine, Butterworth Scientific. Guildford, GB, vol. 21, No. 21-22, Jun. 20, 2003, pp. 3003-3010, XP004429701 ISSN: 0264-410X.
Kapikian Albert Z et al: "A hexavalent human rotavirus-bovine rotavirus (UK) reassortant vaccine designed for use in developing countries and delivered in a schedule with the potential to eliminate the rick of intussusception," The Journal of Infectious Diseases Sep. 1, 2005, vol. 192 Suppl 1, Sep. 1, 2005, pp. S22-S29, XP002416958 ISSN: 0022-1899.

* cited by examiner

*Primary Examiner* — Benjamin P Blumel
(74) *Attorney, Agent, or Firm* — Kilpatrick Townsend & Stockton LLP

(57) ABSTRACT

The present invention provides vaccine compositions for protection against human rotaviral disease designed for use in particular areas of the world. Human× bovine reassortant rotavirus comprising each of the four clinically most important VP7 serotypes of human rotavirus are combined with other VP7 serotypes typically found in the area of interest into a multivalent formulation which provides a high degree of infectivity and immunogenicity. Methods and an administration protocol for producing an immunogenic response without producing an increased risk of intussusception are also provided.

9 Claims, 2 Drawing Sheets

FIG. 2

HEXAVALENT BOVINE ROTAVIRUS REASSORTANT COMPOSITION DESIGNED FOR USE IN DEVELOPING COUNTRIES

CROSS-REFERENCES TO RELATED APPLICATIONS

The present application is a U.S. National Phase Application under 35 U.S.C. §371 of International Application No. PCT/US2006/027444, filed on Jul. 7, 2006, which claims priority to United States Provisional Patent Application No. 60/697,435, filed Jul. 7, 2005, the entire disclosures of which are incorporated by reference herein.

BACKGROUND OF THE INVENTION

Rotaviruses are consistently shown to be the single most important cause of severe diarrhea of infants and young children in both developed and developing countries. The consequences of rotavirus diarrhea are staggering as they account for up to 592,000 deaths annually in the under 5-year age group, predominantly in the developing countries (Parashar et al., *Emerg. Infect. Dis.*, 2003, 9:565-572). It has recently been estimated that 1 in 200 children in developing countries will die from rotavirus diarrhea (Glass et al., *Lancet,* 2004, 363:1547-1550). In the United States, in the under 5-year age group, it was estimated that annually rotaviruses are responsible for 2,730,000 episodes of diarrheal illness, 410,000 visits to a physician, 160,000 emergency room visits, 50,000 hospitalizations, and 20 deaths (Tucker et al., *JAMA,* 1998, 279:1371-1376). Thus, the need for a rotavirus vaccine in both developed and developing countries has received national and international endorsement.

An oral, live, attenuated tetravalent rotavirus vaccine has been developed with the goal of inducing an immunologic response that mimicked natural rotavirus infection, especially with regard to induction of immunity at local intestinal sites (Kapikian et al., *J. Infect. Dis.,* 1996, 174 Suppl 1:S65-72). This tetravalent vaccine was formulated to protect against the four epidemiologically important serotypes, numbered 1-4. Although the relative importance of homotypic vs. heterotypic immunity had not been established with certainty, it appeared from epidemiologic, clinical, animal, and laboratory observations that serotype-specific immunity was a major correlate of protection against rotavirus illness (Hoshino and Kapikian, *J. Health Popul. Nutr.,* 2000, 18:5-14; Jiang et al., *Clin. Infect. Dis.,* 2002, 34:1351-1361). The vaccine was comprised of representatives of each of 4 serotypes: rhesus rotavirus (RRV) which is a VP7 serotype 3 strain, (the Jennerian approach), and three human rotavirus-RRV reassortants, each possessing ten RRV genes and a single human rotavirus gene that encodes VP7 (a major outer capsid protein) that is responsible for serotype 1, 2, or 4 specificity (the modified Jennerian approach) (Kapikian et al., *J. Infect. Dis.,* 1996, 174 Suppl 1:S65-72; Midthun et al., *J. Virol.* 1985, 53:949-954; Midthun et al., *J. Clin. Microbiol.* 1986, 24:822-826). Extensive clinical studies demonstrated the candidate vaccine's safety, immunogenicity and efficacy, especially against severe diarrhea (up to 91% efficacy) (Bernstein et al., *JAMA,* 1995, 273:1191-1196; Perez-Schael et al., *N. Engl. J. Med.,* 1997, 337:1181-1187; Joensuu et al., *Lancet* 1997, 350:1205-1209; Santosham et al., *J. Pediatr.* 1997, 131:632-638, Rennels et al., United States Rotavirus Vaccine Efficacy Group. Pediatrics, 1996, 97:7-13). The vaccine protected against VP7 serotypes 1, 3, and 4 but could not be assessed for VP7 serotype 2 protection because of a paucity of such circulating strains in any of the major field trials (Bernstein et al., *JAMA,* 1995, 273:1191-1196; Perez-Schael et al., *N. Engl. J. Med.,* 1997, 337:1181-1187; Joensuu et al., *Lancet* 1997, 350:1205-1209; Santosham et al., *J. Pediatr.* 1997, 131:632-638; Rennels et al., United States Rotavirus Vaccine Efficacy Group. Pediatrics, 1996, 97:7-13). In addition, in comparative trials of vaccine efficacy, the tetravalent vaccine induced a higher degree of protection, overall, than a monovalent vaccine when the infecting serotype was heterotypic to that of the monovalent vaccine (Bernstein et al., *JAMA,* 1995, 273:1191-1196; Santosham et al., *J. Pediatr.* 1997, 131:632-638; Rennels et al., United States Rotavirus Vaccine Efficacy Group. Pediatrics, 1996, 97:7-13).

The U.S. Advisory Committee on Immunization Practices (ACIP) recommended routine administration of the tetravalent vaccine to infants at 2, 4, and 6 months of age (Recommendations of the Advisory Committee on Immunization Practices (ACIP), MMWR, 1999, 48:all (1-20)). Subsequently, in August 1998, the U.S. Food and Drug Administration (FDA) granted a Biologics License for the vaccine (RotaShield™) to Wyeth Laboratories (Recommendations of the Advisory Committee on Immunization Practices (ACIP), MMWR, 1999, 48:all(1-20)). However, in July 1999, after over one million doses of the vaccine had been given, the U.S. Centers for Disease Control and Prevention (CDC) recommended suspending its further use pending additional studies because of a link with intussusception, especially in the first two weeks after the first dose. Approximately 3 months later, after reviewing additional data, the ACIP withdrew its recommendation for use of the vaccine.

This decision has continued to generate intense discussion and controversy in the scientific community because of continuing disagreements about the actual magnitude of the risk of the vaccine with respect to intussusception and because of related risk-benefit issues. These debates are fueled by the realization that up to approximately 1600 infants and young children worldwide die daily from a disease that might be prevented if RotaShield™ were available for these settings and by the reality that developing countries will not use a vaccine that has been withdrawn for safety reasons in the U.S. Data from CDC indicated initially that the excess risk of intussusception occurring after RotaShield™ was given, was as great as 1.8 based on a case-control study (i.e., up to an 80% excess in the number of cases over background, which corresponds to 1 excess case per 2500 vaccines). From these estimates CDC projected that in a full national vaccination program in the U.S. there would be up to 1600 excess cases over the background estimate of 2000 cases. However, the relative risk figures have undergone considerable downward revisions including estimates of: (i) 1:10,000 excess cases as a consensus figure; (ii) 1:32,000-1:302,000 excess cases in 45-210 day old infants in population-based hospital discharge studies; and (iii) no increase in the number of hospitalizations from intussusception in the under one year age group because of a likely compensatory decrease.

More recently, age at vaccination was shown to be an important factor in the development of intussusception as vaccines who were 90 days of age or older at first dose experienced a disproportionately greater number of cases (81%) than infants who were <90 days of age, with no cases in infants vaccinated at <60 days of age during the two weeks after the first dose in CDC's case-control study. According to analysis of the CDC National Immunization Survey in the 19 states of the case-control study, the ≧90 day old age group had received 38% of all first doses and in addition, the <60 day old group received 16% (approximately 70,000 infants) of all first doses. Thus "catch-up" vaccination of older infants (first dose given to infants beyond the ideally recommended age of two months) was responsible for a substantial portion of the intussusception cases observed in this study.

Concurrent with the development of human rotavirus-RRV reassortants described above, single gene substitution human rotavirus-bovine rotavirus (UK) reassortants have been developed that comprise 10 genes from the bovine (UK) strain and a gene that encodes VP7 the major outer capsid protein for each of the human rotavirus serotype 1, 2, 3, or 4 strains (Midthun et al, *J. Virol.* 53:949-954 (1985); Midthun et al., *J. Clin. Microbiol.* 24:822-826 (1986)). These reassortant constructs were considered our second-generation vaccine because studies with bovine strain NCDV had demonstrated that NCDV induced febrile reactions significantly less often than did the rhesus rotavirus strain vaccine (Vesikari et al., *J. Infect. Dis.* 153:832-839 (1986)). For example in a direct comparison of febrile responses ($\geq$38° C. or 100.4° F. rectally) following vaccination with monovalent RRV or NCDV, RRV induced a febrile response significantly more often than NCDV (64% vs 17%) (Vesikari et al., supra). This was considered to be an advantage for the bovine strain. In addition, as self-limited febrile episodes were also observed with the tetravalent formulation of the rhesus rotavirus-based vaccine (Bernstein et al., *JAMA* 1995, 273:1191-1196; Perez-Schael et al., *N. Engl. J. Med.* 1997, 337:1181-1187; Joensuu et al., *Lancet* 1997, 350:1205-1209; Santosham et al., *J. Pediatr.* 1997, 131:632-638; Rennels et al., *Pediatrics* 1996, 97:7-13), we continued to pursue the bovine rotavirus (UK)-based tetravalent vaccine actively as the second-generation vaccine.

In order to achieve the goal of introducing the bovine UK-based reassortant vaccine as our second-generation vaccine, we have carried out phase 1, 2 and 3 clinical studies, and as described later, new candidate strains were also generated representing emerging serotypes that could be used in countries where such rotavirus strains were prevalent. These studies have been carried out in stepwise fashion as summarized below:

(1) Studies of the safety and immunogenicity of each of the 4 monovalent human-bovine rotavirus (UK) reassortant strains with VP7-specificity for serotypes 1, 2, 3, or 4, sequentially in adults (one dose), children (one dose) and infants (one or two doses) (Clements-Mann et al., *Vaccine* 1999, 17:2715-2725). Each component demonstrated satisfactory attenuation, safety, infectivity and immunogenicity in the target population of infants 1.5-5.9 months of age;

(2) Studies of the safety and immunogenicity of the 4 serotypes combined into a tetravalent formulation of the human-bovine (UK) reassortant vaccine with VP7 specificity for serotypes 1, 2, 3, and 4, in stepwise fashion in adults (one dose), children (one dose), and infants (three doses) (Clements-Mann et al., *Vaccine* 2001, 19:4676-4684). The tetravalent formulation demonstrated satisfactory attenuation, safety, infectivity and immunogenicity in the target population that received the first dose at 1.5-2.5 months of age. In addition, when given concurrently, the tetravalent formulation did not inhibit antibody responses to DTP, HIb, hepatitis B or oral polio vaccine;

(3) The tetravalent human-bovine (UK) reassortant vaccine was evaluated for safety, immunogenicity, and efficacy in a field trial in Finland employing two sequential doses, one at approximately 2 months and the other at about 4 months of age in approximately 170 vaccines and approximately 85 controls. It was shown to be safe, and in contrast to the tetravalent rhesus rotavirus-based vaccine, which was also being evaluated in Finland concurrently in a study of approximately the same size, it did not induce febrile episodes at a frequency significantly greater than that of the placebo group. The tetravalent human-bovine (UK) vaccine induced over 80% protection against severe rotavirus diarrhea, an efficacy level comparable to that observed with the tetravalent rhesus rotavirus-based vaccine.

BRIEF SUMMARY OF THE INVENTION

The present invention provides immunogenic compositions for protection against human rotaviral disease designed for use in particular areas of the world. Human×bovine reassortant rotavirus comprising each of the four clinically most important VP7 serotypes of human rotavirus are combined with other human VP7 serotypes and or VP4 serotypes typically found in the area of interest into a multivalent formulation which provides a high degree of infectivity and immunogenicity. In a particular embodiment, the composition comprises at least five human rotavirus×bovine UK rotavirus reassortants including a gene encoding the human VP7 serotype 1 antigen, the human VP7 serotype 2 antigen, the human VP7 serotype 3 antigen, the human VP7 serotype 4 antigen, the human VP7 serotype 8 antigen, and can optionally include a gene encoding the human VP7 serotype 9 antigen, and/or the human VP7 serotype 5 antigen. The remaining 10 rotavirus genes are typically derived from the bovine UK rotavirus strain.

A method and an administration protocol for producing an immunogenic response without producing an increased risk of intussusception is also provided. In particular, the method provides for the administration of a rotavirus reassortant immunogenic composition between the ages of 0 and about 4 weeks of age with a second administration between 4 and about 8 weeks of age. Typically, there is at least 3 weeks between the first and second dosage of the rotavirus reassortant composition. Also, no rotavirus reassortant composition should be given after about 8 weeks of age.

BRIEF DESCRIPTION OF THE DRAWINGS

FIG. 2 depicts the elements of a hexavalent human×bovine UK rotavirus reassortant composition designed for regions where VP7 serotype 8 and VP7 serotype 9 have become prevalent in addition to the most common VP7 serotypes VP7 serotype 1, serotype 2, serotype 3 and serotype 4.

DETAILED DESCRIPTION OF THE INVENTION

Figure 1:
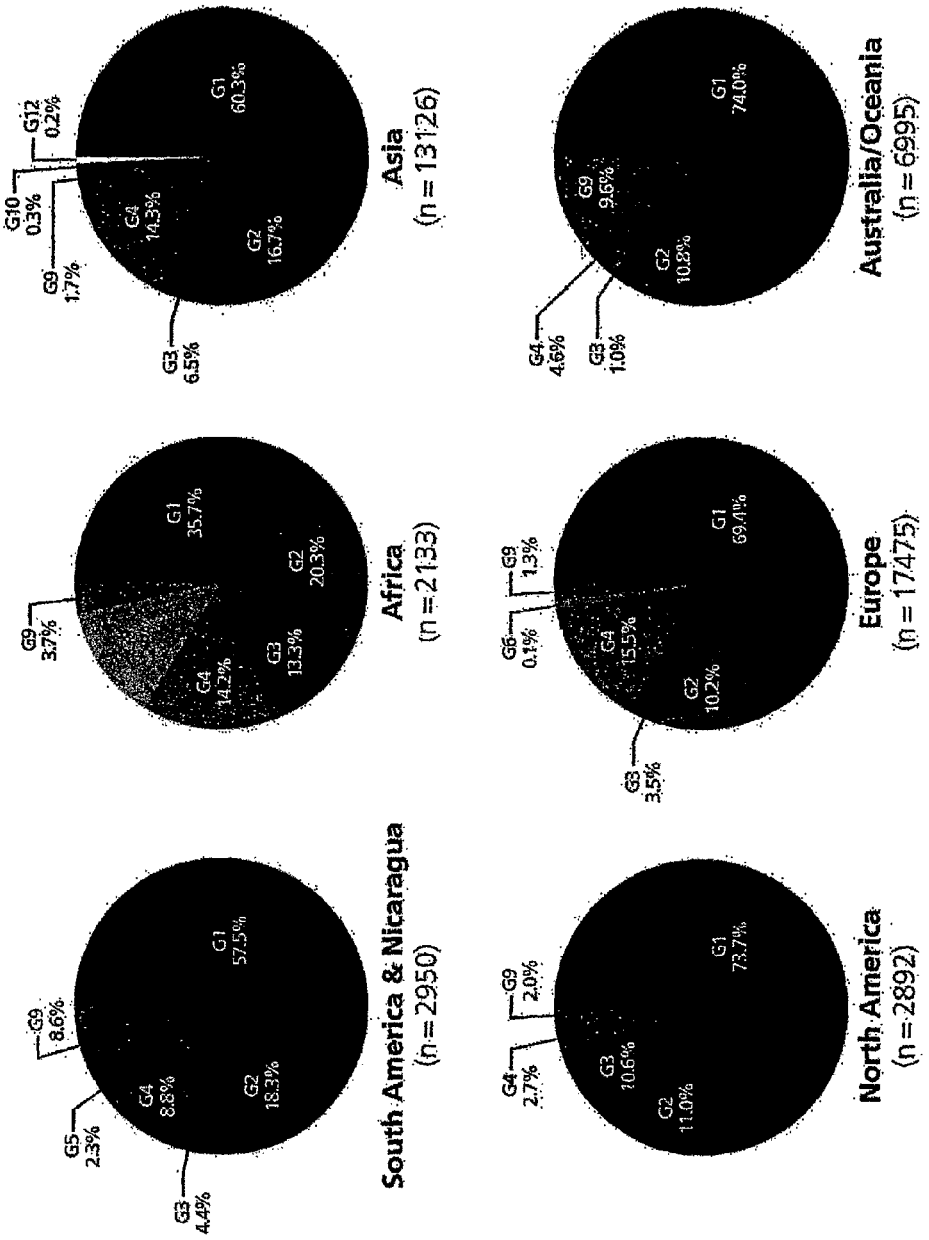
FIG. 1 depicts the distribution of human Group A rotavirus G serotypes in various regions of the world.

In addition to the human-bovine (UK) rotavirus reassortants encoding human VP7 serotypes 1 through 4, various single gene substitution human-bovine (UK) rotavirus reassortants have been developed with a gene of human rotavirus origin encoding VP7 serotype 5, 8, or 9 specificity or VP4 serotype 1A or 1B specificity in a background of ten UK genes ((Hoshino et al., *Vaccine* 2003, 21:3003-3010; Hoshino et al., *Vaccine* 2002, 20:3576-3584; Eichelberger et al., *J. Med. Virol.* 2002, 66:407-416). Similarly, a single gene substitution bovine-bovine (UK) rotavirus reassortant with a gene of bovine rotavirus origin encoding VP7 serotype 10 specificity in a background of 10 UK genes has been developed (Hoshino et al., *Vaccine* 2003, 21:3003-3010). The availability of such reassortants affords the opportunity to formulate "designer vaccines" for specific areas of the world to protect against emerging or unique strains in focal areas of the world. The emergence of unique strains in various parts of the world, as well as the distribution of VP7 (also designated as G (for glycoprotein)) 1 through 4 serotypes is shown in FIG. 1 (Santos and Hoshino, *Rev. Mediacl Virol.* 2005, 15:29-56). For example, G9 strains are now known to be commonly occurring serotypes in numerous developing countries in Asia and Africa (Santos and Hoshino, *Rev. Mediacl Virol.* 2005, 15:29-56). In addition, in a recent study in Australia, G9 strains were found to be the most frequently occurring serotype (Kirkwood et al., *Commun. Dis. Intell.* 2002, 26:537-540). Moreover, G8 strains have also emerged as important strains in various parts of Africa (Santos and Hoshino, *Rev. Medical Virol.* 2005, 15:29-56). G5 strains, which were common in Brazil in the 1990's have decreased in prominence where as G10 strains have maintained a low prevalence (Santos and Hoshino, *Rev. Medical Virol.* 2005, 15:29-56). Although the VP4 (also designated as P (protease sensitive)) 1A serotype is detected in conjunction with various G serotypes, the inconsistency of the association in certain G strains (Santos and Hoshino, *Rev. Medical Virol.* 2005, 15:29-56), indicates to us, that inclusion of prevalent G serotypes would be more practical and effective for inclusion in a multivalent immunogenic composition.

Thus, the immunogenic compositions of the invention specifically comprise a combination of reassortant human×bovine rotaviruses and a physiologically acceptable carrier to form a multivalent composition. In a particular embodiment, the multivalent immunogenic composition comprises a combination of the four reassortant human×bovine rotaviruses of the characteristically most common clinically relevant serotypes of human rotavirus and will further include at least two clinically relevant serotypes of human rotaviruses that occur in focal areas of the world, to form at least a hexavalent immunogenic composition. The immunogenic composition is administered in an immunogenically sufficient amount to an individual in need of immunological protection against rotavirus, such as, e.g., an infant, child or adult. The composition elicits the production of an immune response that is at least partially protective against symptoms of serious rotaviral disease, such as severe diarrhea and dehydration, when the individual is subsequently infected with a wild-type human rotavirus strain. As the reasserted viruses of the immunogenic composition infect the host alimentary tract, some mild disease may occur as a result of the vaccination, but typically the immunogenic composition of the present invention will not cause clinically relevant fever or reaction in the vaccine. Following administration, there are detectable levels of host engendered serum antibodies which are capable of neutralizing the serotypes of rotavirus that make up the immunogenic composition. In particular, the multivalent immunogenic composition of the present invention comprising at least six rotavirus reassortants will produce an immunological response to most, if not all, of the clinically relevant group A human rotaviruses prevalent in each selected different setting.

The reasserted rotavirus which is a component of the multivalent immunogenic composition of the present invention is in an isolated and typically purified form. By isolated is meant to refer to reasserted rotavirus that has been separated from other cellular and viral products of its manufacture, such as wild type virus and other heterologous components of a cell culture or other systems.

Generally, rotavirus reassortants are produced by coinfection of mammalian cells in culture with a tissue culture-adapted animal rotavirus, i.e., bovine, rhesus, and the like, and a tissue culture-adapted human rotavirus. Typically, African green monkey kidney (AGMK) cells are used as the host cells for co-infection. Following co-infection with the animal and human rotavirus strains, selection of the desired reassortant is typically achieved by exposing the growth yield of co-infected cultures to neutralizing antibodies specific for the protein product of the animal rotavirus gene that is to be replaced by the human rotavirus gene (See, U.S. Pat. No. 4,571,385, incorporated herein by reference). In particular, polyclonal serum or monoclonal antibody specific for bovine rotavirus VP7 and/or VP4 proteins can be used. After several rounds of plaque purification and subculture, selected reassortants are characterized for serotype and genotype. Serotype is typically determined by plaque reduction neutralization (PRN) assay or enzyme immunoassay. Genotype is typically determined by gel electrophoresis and RNA-RNA hybridization of the viral genome. Rotavirus reassortants having only the human VP7 (or VP4) gene are typically selected for the present multivalent immunogenic compositions. Reassortants comprising multiple human rotavirus genes can also be used. In this regard, reassortant rotaviruses of interest are particularly those encoding the human rotavirus VP7 and/or the human rotavirus VP4 P1A and or P1B gene products.

In the present invention, particularly preferred rotavirus reassortants are human rotavirus and bovine UK rotavirus reassortants comprising the human rotavirus gene encoding VP7 and the remaining ten rotavirus genes of bovine UK rotavirus origin. The bovine rotavirus strain UK (Woode et al., Res. Vet. Sci. 16:102-105 (1974); Bridger and Woode, Br. Vet. J., 131:528-535 (1975)) is particularly preferred because of its pedigree and as demonstrated by the present invention its higher level of infectivity in humans. Other animal rotavirus strains can also be used to make reassortant rotavirus as long as the compositions are capable of inducing a serologic response in a vaccine when administered at an immunologically effective dosage for each rotavirus serotype. In certain embodiments of the present invention the immunogenic composition comprises less than $10^6$ pfu of each rotavirus VP7 and/or VP4 serotype and they typically do not produce a transient low level febrile response in a vaccine. For example, in certain embodiments the reassortant rotavirus comprises 10 genes from the bovine UK rotavirus strain and a VP7 gene encoding an animal VP7 antigen which is immunologically cross-reactive with human VP7 serotype 10. This reassortant rotavirus can be, for example a bovine×bovine reassortant.

In an alternative embodiment, reassortant rotavirus of a specific serotype can be produced using a previously obtained reassortant. For example, to produce additional bovine UK reassortants a human rotavirus VP7 serotype 1, such as the D strain×bovine UK reassortant HD/BRV-1 (ATCC VR-2069) can be used to produce human rotavirus×bovine UK reassortants having human VP7 serotypes of 2, 3, 4, 5, 8, 9, and/or bovine rotavirus VP7 serotype 10. The methods used are similar to those described above except polyclonal or monoclonal neutralizing antibody specific for the VP7 serotype of the parental human rotavirus reassortant is used to select for the new reassortants comprising the desired human (and/or bovine) rotavirus VP7 serotype.

Propagation of the reassorted rotavirus can 0be in a number of cell cultures which support rotavirus growth. Preferred cell cultures for propagation of rotavirus reassortants for vaccine use include primary or secondary simian African green monkey kidney cells (AGMK), qualified diploid simian FRhL-2 cells and qualified simian heteroploid Vero cells. Cells are typically inoculated with rotavirus reassortants at a multiplicity of infection ranging from about 0.1 to 1.0 per cell, or more, and are cultivated under conditions appropriate for viral replication, for about 3-5 days, or as long as necessary for virus to reach an adequate titer. Rotavirus reassortants are harvested from infected cell culture and separated from cellular components, typically by well known clarification procedures, e.g., centrifugation, and may be purified as desired using procedures well known to those skilled in the art.

Rotavirus strains useful in constructing the bovine reassortant rotavirus of the present invention include, for example, human rotavirus IAL28 (P1A[8], serotype 5 (Timenetsky et al., *J. General Virol.* 1997, 78:1373-1378)), human rotavirus strain 1290 (P[4] serotype 8 (Nakata et al., *J. Med. Virol.* 1999, 58:296-303)), human rotavirus strain AU32 ((P1A[8], serotype 9 (Nakagomi et al., *Microbiol. Immunol.*, 1990, 34:77-82)), bovine rotavirus strain KC-1 (P8[11], serotype 10) which is cross reactive with human rotavirus serotype 10, and/or human rotavirus having the VP4 1A serotype and/or the VP4 1B serotype (Hoshino et al., *Vaccine* 2002, 20:3576-3584).

Figure 2:
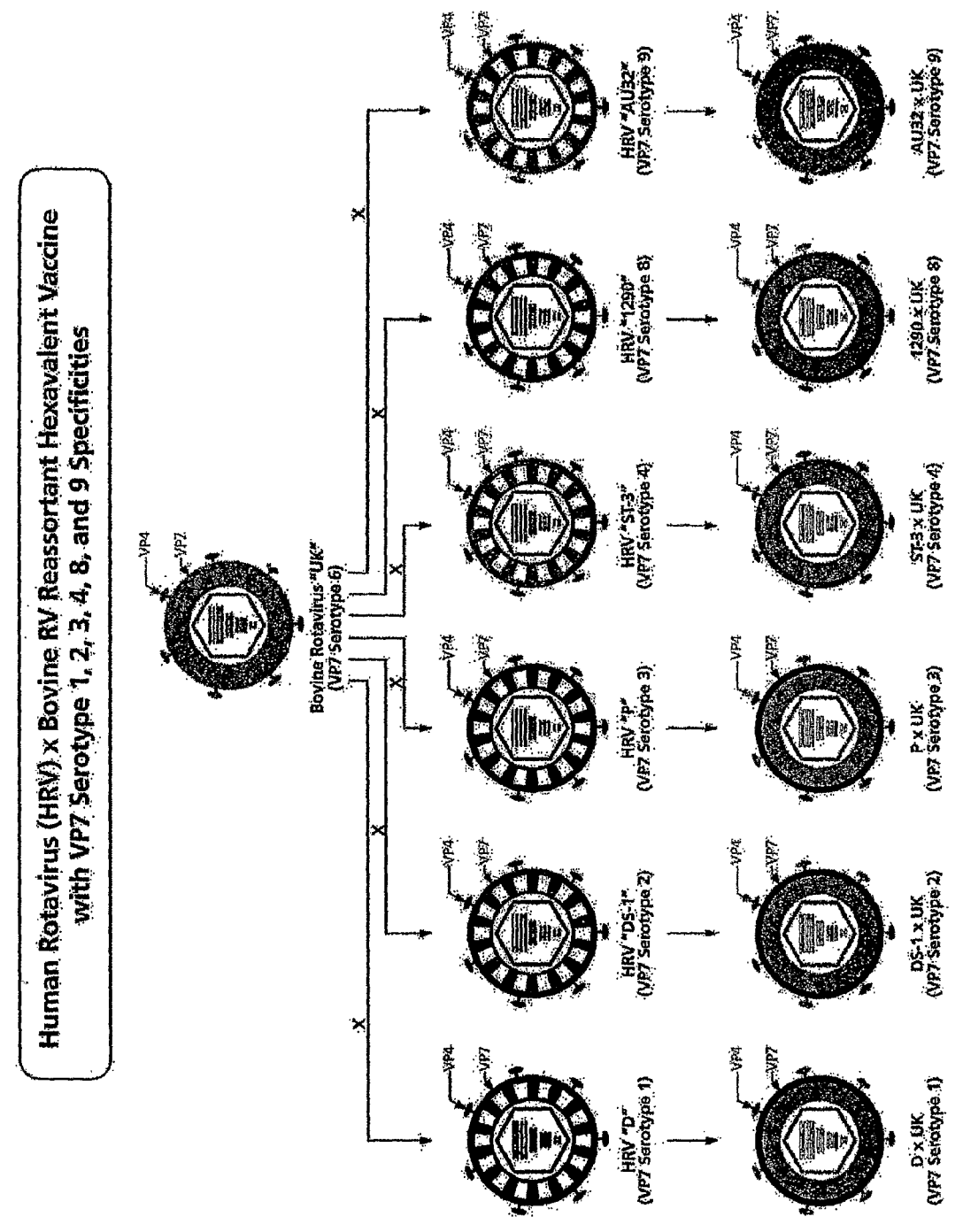

In a typical embodiment of an immunogenic composition of the present invention, a human×bovine reassortant rotavirus of serotype 1, serotype 2, serotype 3, serotype 4, serotype 8, and serotype 9 are used as a hexavalent vaccine. Typically, the human×bovine reassortant rotavirus of each of the six serotypes will be admixed to form a combined composition for simultaneous administration. The elements of such a composition is shown in FIG. 2. The effect of adding two additional serotypes to the tetravalent formulation can be evaluated with regard to (i) interference among the strains that might influence immunogenicity, and (ii) the increased cost of manufacturing a hexavalent vaccine. The final ratio of each rotavirus serotype is determined by the immunogenicity of the individual rotavirus reassortants. Although not preferred, each human×bovine reassortant, or a combination thereof, can also be administered in a sequential manner to provide an effective vaccine formulation.

In other embodiments of the present invention the human×bovine reassortant rotavirus of serotype 1, serotype 2, serotype 3, and serotype 4, are combined with a human×bovine reassortant rotavirus of VP7 serotype 5, and/or serotype 8 and/or serotype 9 and/or serotype 10, such as, for example, a bovine×bovine reassortant rotavirus of VP7 serotype 10 which is immunologically cross-reactive with human VP7 serotype 10, and/or a human×bovine reassortant rotavirus of VP4 serotype 1A and/or 1B to yield a multivalent immunogenic composition. The exact composition of the multivalent immunogenic composition depends on the strains of rotavirus prevalent in an area of interest. The additional reassortant rotaviruses just described can be used in any combination for use as a hexavalent, septavalent, or octavalent immunogenic composition.

Human×bovine reassortant rotavirus multivalent immunogenic compositions of the present invention contain as an active ingredient an immunogenically effective amount of each of at least the four clinically most important VP7 serotypes of human rotavirus as described herein. In one particular embodiment of the present invention, each antigenically distinct human rotavirus reassortant is administered at a dosage of less than $10^{6.0}$ plaque forming units. The immunogenic composition may be introduced into a host, particularly humans, with a physiologically acceptable carrier and/or adjuvant. Useful carriers include, e.g., citrate-bicarbonate buffer, buffered water, normal saline, and the like. The resulting aqueous solutions may be packaged for use as is, or lyophilized, as desired, using lyophilization protocols well known to the artisan. Lyophilized virus will typically be maintained at about 4° C. When ready for use the lyophilized preparation is combined with a sterile solution prior to administration, as mentioned above.

The compositions may contain pharmaceutically acceptable auxiliary substances as required to approximate physiological conditions, such as pH adjusting and buffering agents and the like, for example, sodium acetate, sodium lactate, sodium chloride, potassium chloride, calcium chloride, sorbitan monolaurate, tri-ethanolamine oleate, citrate-bicarbonate, or the like. Typically, the composition is administered orally and therefore it may also be necessary to provide the individual a buffer solution to partially neutralize stomach acid and protect the reassortant rotavirus while passing to the intestine. Buffer solutions appropriate for this use include sodium bicarbonate, citrate bicarbonate, or the like. Upon immunization with a multivalent human×bovine reassortant rotavirus composition of the present invention, particularly via the oral route, the immune system of the host responds to the composition by producing both local secretory and serum antibodies specific for the rotavirus proteins. As a result of the administration of the composition, the host becomes at least partially or completely immune to human rotavirus disease caused by a wild-type strain that corresponds to the immunizing serotype(s). If wild-type virus infection does occur, the host is resistant to developing moderate or severe rotaviral disease, particularly of the gastrointestinal tract.

Typically, the multivalent immunogenic compositions of the present invention containing the human×bovine reassortant rotaviruses are administered to a person, particularly an infant, susceptible to or otherwise at risk of rotavirus disease to induce the individual's own immune response capabilities. Such an amount is defined to be an "immunogenically effective dose." Immunogenic or "immunogenically effective dose" as used in the present invention means the development in a vaccine of a cellular and/or antibody mediated immune response to the immunogenic composition of the present invention. Usually such a response consists of the vaccine producing serum antibodies, B cells, helper T cells, suppressor T cells, and/or cytotoxic T cells directed specifically to an antigen or antigens included in the vaccine composition of the present invention. A four-fold or greater rise above a preinoculation antibody titer following immunization measured by a rotavirus group-specific, or rotavirus serotype-specific assay is considered a significant response.

In this use, the precise amount of each human×bovine reassortant rotaviral serotype in a particular immunogenic composition depends on the patient's age, state of health and weight, the mode of administration, the nature of the formulation, and the like, but generally the range is from about $10^4$ to about $10^{10}$ plaque forming units. Typically the composition is administered at a dosage of from about $10^4$ to less than $10^6$ plaque forming units (pfu) of each serotype per dose per patient.

In any event, the formulations for the immunogenic composition should provide a quantity of each human×bovine reassortant rotavirus of the invention sufficient to induce an individual's immune response against rotavirus disease. Preferably, this immune response will effectively protect the individual against serious or life-threatening rotavirus disease without being "reactogenic." As used herein, "reactogenic" or reactogenicity denote a mild transient fever occurring during the week following administration of the immunogenic composition. A fever is defined in the context of the present invention as the development of an oral or rectal temperature of greater than or equal to 38° C. in an adult, or in a pediatric vaccine.

In some instances it may be advantageous to combine the multivalent bovine reassortant rotaviral compositions of the present invention with other infectious agents, particularly, other gastrointestinal viruses. For example, the hexavalent human×bovine reassortant rotaviral composition of the present invention can further include, for example, administration either simultaneously (but typically separately) or sequentially with another possible gastrointestinal virus vaccine, such as a human calicivirus (e.g., Norwalk virus) or a related vaccine.

Single or multiple administrations of the immunogenic compositions of the invention can be carried out. In neonates and infants, multiple administrations may be required to elicit a sufficient level of immunity, particularly where there are high levels of maternally derived antibodies specific for rotavirus. Administration should begin within the first 0-4 weeks of life, and continue at intervals such as three weeks after the initial immunization, or as necessary to induce and maintain sufficient levels of immunity against human rotavirus infection. But, typically no administration after 8 weeks to avoid the potential for intussusception. Similarly, adults who are particularly susceptible to repeated or serious rotavirus disease, such as, for example, health care workers, day care workers, family members of young children, the elderly, and the like, may require multiple immunizations to establish and/or maintain an effective immune response. Levels of induced immunity can be monitored by measuring amounts of rotavirus group-specific antibodies or serotype-specific neutralizing antibodies in serum and secretions, and dosages adjusted or vaccinations repeated with one or more serotypes of a multivalent reassortant rotavirus composition of the present invention when necessary to maintain desired levels of immunity.

The present invention also provides a revised schedule for the administration of the bovine rotavirus-based immunogenic compositions of the present invention that may eliminate the risk of excess cases of intussusception following administration. Prior to the present invention it was known that naturally-occurring intussusception is relatively infrequent in the first two months of life (Parashar et al., *Pediatrics* 2002, 106:1413-1421) and characteristically peaks in the 4 to 9 month age group as documented for an almost 7 year period in a California Managed Care Organization (Chang et al., *Pediatr. Infect. Dis.* 2002, 21:97-102). A World Health Organization (WHO) report has indicated that in Africa, Asia, the Eastern Mediterranean, Central and South America, and in Europe, the median peak incidence of intussusception occurred between 3 and 8 months of age (Bines and Ivanoff, IWHO/V&B/02.19 (2002)). In view of the recent findings in the U.S. that there was a disproportionate occurrence of intussusception associated with "catch-up" vaccination in the ≧90 day old infant age group and no cases in the <60 day old age group within two weeks of receiving the first dose, the present invention provides for the administration of, for example, the hexavalent bovine rotavirus-based immunogenic composition in a two-dose regimen with the first dose at 0 to 4 weeks of age and the second dose at 4 to 8 weeks of age with a minimum of three weeks between the first and second doses. There would be no "catch-up" vaccinations after eight weeks of age (i.e., no first or second doses given beyond eight weeks of age) to avoid vaccination during the highly vulnerable period. In this way, the peak period of vulnerability for developing intussusception under natural conditions (i.e., about 3 or 4 to 9 months of age) would be avoided, and the occurrence of vaccine-induced intussusception following either the first or second dose should be eliminated.

A two-dose schedule beginning in the first month of life should induce satisfactory protection against severe rotavirus diarrhea. Immunogenicity and/or efficacy trials can be carried out to further test the result. Evidence from various studies appears to be suggest a successful outcome for such trials. For example: (1) naturally-occurring subclinical neonatal rotavirus infection induced protection against severe rotavirus diarrhea in Australia (Bishop et al., *N. Engl. J. Med.* 1983, 309: 72-77; (2) infants studied in Mexico from birth to 2 years of age were protected (87%) against moderate-to-severe diarrhea after one naturally-occurring rotavirus infections in Mexico (Velazquez et al., *N. Engl. J. Med.* 1996, 14:1022-1028; (3) neonatal rotavirus vaccination with RIT 4237 bovine (NCDV) rotavirus vaccine modified the severity of rotavirus gastroenteritis in Finland (Vesikari et al., *Pediatr. Infect. Dis. J.* 1987, 6:164-169); and (4) a neonatal dose of tetravalent rhesus rotavirus-based vaccine protected against the occurrence of fever associated with the second vaccine dose at 2 months of age (Vesikari et al., *Abstracts of the Infectious Diseases Society of America* 37th *Meeting*, Abstract 649, p. 1075 (1999)).

With this 0 to 4 and 4 to 8 week two dose schedule, the risk of post-vaccination intussusception may be eliminated, and a further benefit may follow, such as for example, the vaccine may prevent intussusception due to wild type rotavirus (Murphy et al., *J. Infect. Dis.* 2003, 187:1301-1308; Nakagomi, *N. Engl. J. Med.* 2001, 344:1866). However, only large-scale post-licensure phase 4 studies will answer whether this schedule will eliminate or significantly reduce the risk of vaccine-associated intussusception. Although studies of the association of wild-type rotavirus infection with intussusception have yielded variable results (Chang et al., *Pediatr. Infect. Dis. J.* 2002, 21:97-102; Bines and Ivanoff, supra; Konno et al., *J. Med. Virol.* 1978, 2:265-269; Nakagomi, *Microbiol. Immunol.* 2000, 44:619-628), recent intestinal ultrasound studies showed that wild type rotavirus induced a significantly greater number of lymph node aggregates and significantly greater thickening of the distal ileum—pathologic alterations that may be a prelude to intussusception—than observed in control infants in coded examinations (Robinson et al., *J, Infect. Dis.* 2004, 189:1382-1387). There is no assurance that when one million doses of other rotavirus vaccines are given that they will not be linked to rare cases of intussusception especially when given in "catch-up" situations. Thus, the suggested schedule described above has the potential to eliminate, or at least significantly decrease, the risk of intussusception linked to rotavirus vaccination.

Conclusion

A revised schedule of administration is provided for the disclosed bovine rotavirus-based vaccine which has the potential of eliminating the risk of intussusception because the vaccine would be administered during a period when infants are relatively refractory to the development of intussusception, i.e., at 0 to 8 weeks of age. In addition, we are proposing the use of a hexavalent bovine rotavirus (UK)-based vaccine for developing countries to cover not only the standard serotypes G1 through G4 but also emerging serotypes G8 and G9. Additional embodiments are provided which can add the G5 and/or G10 serotypes in addition to the G8 and/or G9 serotypes or in any combination depending on the serotype of rotavirus endemic to the particular area of interest. A similar schedule and formulation may facilitate the re-introduction of RotaShield™, as serotype G8 and G9 reassortants are also available for this vaccine (Hoshino et al., *Vaccine* 2003, 21:3003-3010). RotaShield™ has the advantage that over one million doses have been given to approximately 600,000 infants, whereas, the bovine (UK) rotavirus-based vaccine has undergone only limited clinical trials. However, the bovine (UK) rotavirus-based vaccine has the advantage of being associated with significantly fewer febrile responses. It would be of great importance and benefit if rotavirus vaccines could be used safely in infancy, especially in the developing countries where the consequences of rotavirus infection are so devastating.

The following examples are offered by way of illustration, not by way of limitation.

EXAMPLES

This Example describes the evaluation of the safety, immunogenicity and reactogenicity of each reassortant of a multivalent bovine reassortant immunogenic composition individually in adults, children, and infants. The composition comprises the human×bovine UK rotavirus reassortants representing the VP7 serotypes 1, 2, 3, 4, 8 and 9. Additional compositions can include the VP7 gene from human IAL28 representing serotype 5 and/or the VP7 gene from bovine rotavirus strain KC-1 which is an immunologically cross-reactive with human rotavirus VP7 serotype 10.

One embodiment of the invention comprises the human× bovine reassortant rotavirus strains representing VP7 serotypes 1, 2, 3, 4, 8 and 9 that were derived from the bovine UK Compton (UK) strain and from human rotavirus strains D (VP7 serotype 1, ATCC VR-970), DS-1 (VP7 serotype 2; Wyatt et al., *Perspect. Virol.* 1978, 10:121-145), P (VP7 serotype 3; Wyatt et al., *Science* 1983, 207:189-171), ST3 (VP7 serotype 4; Banatvala et al., *J. Am. Vet. Med. Assoc.* 1978, 173:527-530), 1290 (VP7 serotype 8; Nakata et al., *J. Med. Virol.* 1999, 58:296-303), and AU32 (VP7 serotype 9; Nakagomi et al., *Microbiol. Immunol.,* 1990, 34:77-82)). The bovine UK Compton rotavirus strain was isolated in primary calf kidney cells from the stool of a colostrum-deprived calf with diarrhea. (Woode et al., *Res. Vet. Sci.* 1974, 16:102-105).

The individual human×bovine rotavirus reassortants with a single VP7 encoding gene derived from human rotavirus D, DS-1, P, ST3, IAL28, 1290, or AU32 strain and the remaining 10 genes derived from the bovine UK strain (lot BR-3, clone 22) have been described (Midthun et al., *J. Clin. Microbiol.* 1986, 24:822-826; Midthun et al., *J. Virol.* 1985, 53:949-954; U.S. Pat. No. 4,571,385; and Hoshino et al., *Vaccine* 2003, 21:3003-3010, all of which are incorporated herein by reference). The D×UK, DS-1×UK, P×UK and ST3×UK vaccine suspensions used in these clinical trials, i.e., lot HD BRV-1, clone 47-1-1 (ATCC VR-2069 and ATCC VR-2617), $10^{5.8}$ pfu/ml; lot HDS1 BRV-1, clone 66-1-1 (ATCC VR-2616), $10^{5.3}$ pfu/ml; lot HP BRV-2, clone 22-1-1 (ATCC VR-2611), $10^{5.3}$; and lot ST3 BRV-2, clone 52-1-1 (ATCC VR-2612), $10^{5.8}$ pfu/ml respectively, as well as IAL28×UK, 1290×UK and AU32×UK, can be prepared and successfully safety tested to confirm freedom from known adventitious agents in accordance with the guidelines of the U.S. Food and Drug Administration as well known to the skilled artisan.

All studies should be conducted in a randomized, placebo-controlled manner to assess the safety and immunogenicity of each candidate rotavirus vaccine strain. The safety of each human×bovine reassortant rotavirus can be evaluated sequentially in adults 18 to 45 years of age, and in infants 0 to 4 weeks of age.

The criteria for selection of adult and pediatric patients for rotavirus vaccine trials have been described in Halsey et al., (*J. Infect. Dis.* 1988, 158:1261-1267). An undiluted dose of each rotavirus reassortant is typically evaluated in adults initially. Subsequently, a 1:10 dilution of each reassortant and later an undiluted dose of the composition can be evaluated in children 6 to 60 months of age. After the safety of each reassortant has been demonstrated in these children, a 1:10 dose and an undiluted dose of each composition can be evaluated sequentially in infants <4 weeks old. The testing of children in the 6 to 60 month age group can be carried out where the clinical benefit greatly exceeds the risk of intussusception. Since it appeared in earlier studies that an undiluted dose of these reassortants was required to infect the majority of the young infants, the P×UK or ST3×UK reassortant can be administered undiluted to infants <6 months old when combined with other human×bovine UK rotavirus reassortants.

Initially, the safety of the reassortant rotavirus strain is evaluated in healthy adult volunteers who possess neutralizing antibodies in their serum specific for the VP7 serotype of the immunizing rotavirus strain. The clinical procedures for the studies with adults can be those previously described in Halsey et al., supra, with a few typical exceptions. Briefly, all subjects are fasted for at least 1 hour before and after each feeding of rotavirus. Each adult volunteer will drink about 120 ml of distilled water with 2 g of $NaHCO_3$, followed about 1 min. later by 1 ml of undiluted candidate vaccine suspended in 30 ml of buffered solution or 31 ml of placebo (buffered solution without the vaccine). Oral temperature is recorded twice daily and any elevated temperature rechecked within 20 minutes. Stool samples are collected for 7 days following the administration of rotavirus and the consistency and number of stools recorded and any symptoms also recorded daily for 7 days after vaccination.

Most of the clinical procedures for the pediatric studies are also identical to those described by Halsey et al. (supra.), with some exceptions. Briefly, routine childhood immunizations appropriate for the child's age is given on schedule, and at least two weeks before or after administration of rotavirus or placebo. After fasting one hour, each pediatric subject is randomized to receive rotavirus or placebo in a 2:1 ratio. Each child drinks about 30 ml of infant formula (Similac; Ross Laboratories, Columbus, Ohio) mixed with about 0.4 g of $NaHCO_3$, and then drinks about 1 ml of rotavirus reassortant or placebo (buffered formula or Eagle's Minimal Essential Medium). Infants <2 to about 3 months of age who may be weakly immunogenic are offered a second dose of the virus 4 to 8 weeks after the first dose in an attempt to increase immunogenicity. No "catch-up" vaccinations are to be given.

In these studies, rectal temperatures can be taken once or twice a day, and symptoms, if any, recorded daily. Typically, parents are instructed to collect a stool sample daily and record the number and consistency of stools passed by their child daily. Procedures for pediatric studies can be similar with slight modifications.

Study subjects are considered to have "rotavirus-like illness," (i.e., an illness that could possibly be caused by a rotavirus), if they have diarrhea, or any episode of frank vomiting or fever during the 7-day period after oral administration of rotavirus. Diarrhea is defined as three or more unformed stools within about 48 hours. Fever is defined as an oral temperature $\geq 37.8°$ C. in adults or a rectal temperature $\leq 38.1°$ C. in pediatric subjects, confirmed within 10-20 minutes.

Blood can be collected from each study participant before and 4-6 weeks after administration of rotavirus for measurement of rotavirus-specific antibodies and serum alanine aminotransferase (ALT) level; the latter is typically used to ascertain whether the vaccine adversely affected liver functions. In adults, an additional blood specimen is typically also collected one week after administration of rotavirus and used for measurement of ALT level.

Prevaccination and postvaccination sera are tested for rotavirus-specific IgA and IgG antibodies by ELISA, using rhesus rotavirus as a group-specific antigen as described in Midthun et al., *J. Clin. Microbiol.* 1989, 27:2799-2804 and Hoshino et al., *J. Clin. Microbiol.* 1985, 21:425-430; each incorporated by reference herein. Paired sera are also tested by plaque reduction neutralization (PRN) antibody assay as described in Midthun et al., *J. Clin. Microbiol.* 1989, 27:2799-2804. Rotaviruses used in the PRN assay can include: Wa (serotype 1), DS-1 (serotype 2), P (serotype 3) and ST3 or VA70 (serotype 4), IAL28 (serotype 5), AU32 (serotype 9), 1290 (serotype 4) human rotavirus strains plus: D×UK, DS-1×UK, P×UK, IAL28×UK, AU32×UK, 1290× UK and/or ST3×UK reassortant strains and the UK (Compton) bovine rotavirus strain. A fourfold or greater rise in antibody titer in the postvaccination serum compared to the prevaccination serum measured by ELISA IgA or ELISA IgG, or PRN antibody assay is typically considered a significant response.

Frozen stool samples are also typically thawed and made into 10% stool suspensions in veal infusion broth to test for the presence of virus. The stool suspensions are inoculated onto simian MA104 cell culture tubes and incubated in a roller drum at 37° C. for 7 days. The supernatant from the cell culture is blind passaged onto fresh simian MA104 cell culture tubes and incubated at 37° C. for 7 days. The 10% stool suspension and the supernatants from each set of cultures can be stored at −20° C., until later when they were thawed and tested for rotavirus by ELISA. Selected rotavirus positive stool specimens collected following vaccination are currently serotyped by polymerase chain reaction to determine the serotype of rotavirus shed (Gouvea et al., *J. Clin. Microbiol.* 1990, 28:276-282 and Gouvea et al., *J. Clin. Microbiol.* 1994, 32:1333-1337, each incorporated by reference herein).

Diarrheal stools of study participants can be examined as necessary for ova and parasites, and can also be tested for salmonella, shigella, campylobacter, aeromonas, yersinia, enterovirus, adenovirus, and rotavirus. Diarrheal stools, when tested, are also examined by electron microscopy for rotavirus and other viral particles. To detect adventitious agents associated with intercurrent illness, nasal swabs or nasal wash specimens are collected from study subjects who have fever and respiratory symptoms during the 7-day observation period in the studies, and these specimens are tested in cell culture for respiratory viruses.

The rates of illness of vaccines and placebo recipients and the rates of serologic response for these groups within each age group and in each study are compared using a two-tailed Fisher's exact test. The percentages of adults, children and infants who had rotavirus detected in their stools or developed a fourfold or greater rise in serum antibody titer(s) after a single oral administration of each of the VP7-serotype-specific human× UK bovine rotavirus reassortants are determined.

Microorganism Deposit Information

The human rotavirus strains were deposited with the American Type Culture Collection, 10801 University Boulevard, Manassas, Va. 20110-2209, on the deposit date indicated below, under the conditions of the Budapest Treaty and designated as follows.

| Reassortant Designation | ATCC Accession Number | Deposit Date |
|---|---|---|
| HD x BRV, clone 47-1-1 (VP7:1 [D]) | ATCC VR-2617 | Jun. 4, 1998 |
| HDS1 x BRV-1, clone 66-1-1 (VP7:2 [DS-1]) | ATCC VR-2616 | Jun. 4, 1998 |
| HP x BRV, clone 22-1-1 (VP7:3 [P]) | ATCC VR-2611 | Jun. 4, 1998 |
| HST3 x BRV-2, clone 52-1-1 (VP7:4 [ST3]) | ATCC VR-2612 | Jun. 4, 1998 |
| IAL28 x UK, clone 33-1-1 (VP7:5 [IAL28]) | ATCC VR-2613 | Jun. 4, 1998 |
| AU32 x UK, clone 27-1-1 (VP7:9 [AU32]) | ATCC VR-2614 | Jun. 4, 1998 |
| HRV 1290 x UK (VP7:8 [1290]) | ATCC PTA-6851 | Jul. 8, 2005 |
| KC-1 x UK, clone 32-1-1 (VP7:10 [KC-1]) | ATCC VR-2615 | Jun. 4, 1998 |

Although the foregoing invention has been described in some detail by way of illustration and example for purposes of clarity of understanding, it will be obvious that certain changes and modifications may be practiced within the scope of the appended claims. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A multivalent immunogenic composition comprising at least five different rotavirus reassortants, wherein the composition comprises the rotavirus reassortant of 1290×UK (ATCC PTA-6851) and wherein the composition induces an immune response capable of reducing the clinical symptoms associated with gastroenteritis caused by rotavirus infection.

2. The composition of claim 1, which comprises D×UK (ATCC VR-2617), DS-1×UK (ATCC VR-2616), P×UK (ATCC VR-2611), ST-3×UK (ATCC VR-2612), 1290×UK (ATCC PTA-6851), and AU32×UK (ATCC VR-2614).

3. The composition of claim 2, further comprising IAL28× UK (ATCC VR-2613).

4. The composition of claim 1, further comprising KC-1× UK (ATCC VR-2615).

5. The composition of claims 1, 2, 3 or 4, wherein each rotavirus reassortant is present at an amount of less than $10^6$ plaque forming units (pfu) for each dosage to be administered.

6. The composition of claims 1, 2, 3 or 4 further comprising a human × bovine reassortant rotavirus of human VP4 serotype 1A and/or human VP4 serotype 1B.

7. The composition claim 1, further comprising a physiologically acceptable carrier.

8. The composition of claim 1, further comprising an adjuvant.

9. The composition of claim 1, wherein the composition is lyophilized.

* * * * *